(12) United States Patent
Nakamura et al.

(10) Patent No.: US 6,462,232 B1
(45) Date of Patent: Oct. 8, 2002

(54) PRODUCTION PROCESS FOR ACRYLIC ACID UNDER CONTROLLED TEMPERATURE CONDITIONS

(75) Inventors: Daisuke Nakamura; Hideyuki Hironaka; Michio Tanimoto, all of Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/365,845

(22) Filed: Aug. 3, 1999

(30) Foreign Application Priority Data

Aug. 10, 1998 (JP) ............................................. 10-225753

(51) Int. Cl.$^7$ ........................................... C07C 51/235
(52) U.S. Cl. ...................................................... 562/532
(58) Field of Search ................................ 562/535, 534, 562/532; 560/241, 245

(56) References Cited

U.S. PATENT DOCUMENTS

| | | | |
|---|---|---|---|
| 3,801,634 A | | 4/1974 | Krabetz et al. |
| 4,203,906 A | * | 5/1980 | Takada et al. |
| 4,256,783 A | * | 3/1981 | Takada et al. |
| 4,873,368 A | * | 10/1989 | Kadowaki et al. |
| 5,183,936 A | * | 2/1993 | Etzkorn et al. |
| 5,264,625 A | | 11/1993 | Hammon et al. |
| 5,521,137 A | * | 5/1996 | Martin et al. |
| 5,739,391 A | * | 4/1998 | Ruppel et al. |

FOREIGN PATENT DOCUMENTS

| | | |
|---|---|---|
| DE | 4431949 | 3/1995 |
| EP | 0534294 A | 3/1993 |
| JP | 229984 | 9/1993 |

* cited by examiner

*Primary Examiner*—Gary Geist
*Assistant Examiner*—Robert W. Deemie
(74) *Attorney, Agent, or Firm*—Sherman & Shalloway

(57) ABSTRACT

Provided is a process for producing acrylic acid stably at a high yield over a long period of time by subjecting acrolein or acrolein-containing gas to catalytic vapor phase oxidation. The above process is characterized by controlling the reaction so that the following equations (1) and (2) are satisfied:

Figure 1:
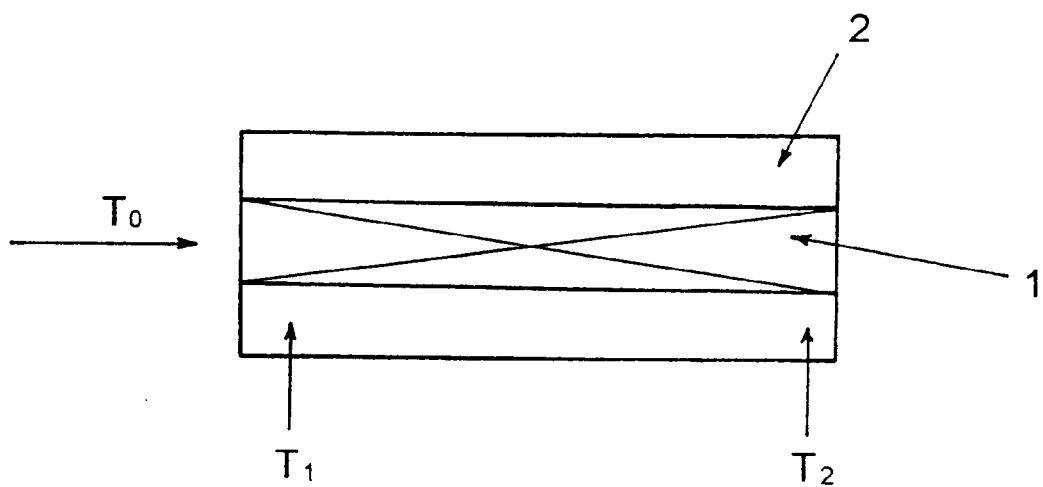

$$1° C. \leq T_0 - T_1 \leq 15° C. \quad (1)$$

$$T_1 < T_2 \quad (2)$$

wherein $T_0$ represents a temperature of acrolein or the acrolein-containing gas in an inlet of a catalyst layer; $T_1$ represents a temperature in an inlet part of the catalyst layer; and $T_2$ represents a temperature in an outlet part of the catalyst layer.

14 Claims, 1 Drawing Sheet

PRODUCTION PROCESS FOR ACRYLIC ACID UNDER CONTROLLED TEMPERATURE CONDITIONS

FIELD OF THE INVENTION

The present invention relates to a production process for acrylic acid. More specifically, the present invention relates to a process for producing acrylic acid stably at a high yield over a long period of time in subjecting acrolein or acrolein-containing gas to vapor phase oxidation with an oxidizing catalyst to produce acrylic acid.

RELATED ART

Acrylic acid is industrially produced on a large scale by a catalytic vapor phase oxidation of acrolein. In this case, acrolein-containing gas obtained by subjecting propylene to vapor phase oxidation with an oxidizing catalyst containing molybdenum and bismuth as essential components is generally used for a reaction raw material as it is or by adding air and steam thereto. Accordingly, acrylic acid is usually produced by so-called two-step reaction comprising a former step for subjecting propylene to catalytic vapor phase oxidation to form acrolein and a latter step for subjecting acrolein-containing gas obtained in this former step to catalytic vapor phase oxidation to produce acrylic acid.

In the two-step reaction described above, however, the acrolein-containing gas obtained in the former step has a high reactivity to bring about an after-reaction at a high temperature, and not only acrolein is oxidized to carbon monooxide and carbon dioxide, but also sudden heat generation and a change in the volume are caused, so that there is a problem in terms of safety. Accordingly, the acrolein-containing gas obtained in the former step is quickly cooled down to a safe temperature at which the after-reaction does not take place.

Accordingly, the acrolein-containing gas fed to the latter step has a lower temperature than the reaction temperature or is heated up to the reaction temperature at most if heated again by pre-heating. The reasons thereof are not only to prevent, as described above, the after-reaction of acrolein but also because of the risk that an introduction of the acrolein-containing gas having a higher temperature than the reaction temperature makes it impossible to sufficiently control the reaction and therefore causes an abnormal reaction such as a run-away reaction.

Disclosed in Japanese Patent Application Laid-Open No. 229984/1993 is an improved reaction temperature program for the purpose of elevating a conversion of acrolein and a selectivity of acrylic acid. It is described therein that acrolein-containing gas is pre-heated to a temperature which is higher by 0 to 20° C. than an inlet temperature of a reaction layer and then introduced into the reaction layer. However, it is an essential requisite in this process that a temperature of the second reaction zone at an outlet side of the reaction layer is lowered than a temperature of the first reaction zone at an inlet side and the reaction temperature is lowered by 5 to 40° C.

PROBLEMS TO BE SOLVED BY THE INVENTION

With respect to a production of acrylic acid from acrolein, it has been a continuous research subject for technicians still now in the technical field concerned to enhance the yield of acrylic acid and lower the product cost thereof. The process described in Japanese Patent Application Laid-Open No. 229984/1993 described above is not yet sufficiently satisfactory.

Thus, an object of the present invention is to provide an improved process for producing acrylic acid from acrolein stably at a high yield over an extended period of time.

MEANS FOR SOLVING THE PROBLEMS

As described above, in the conventional process, the acrolein-containing gas fed to the latter step has a lower temperature than the reaction temperature or is heated up to the reaction temperature at highest if heated again by pre-heating, and therefore the catalyst in the vicinity of a gas inlet in the catalyst layer does not sufficiently display an oxidation function thereof. In other words, the above catalyst layer fulfills a function only as a preheating layer for heating the gas up to the reaction temperature. Intensive investigations continued by the present inventors paying attentions to the above matter have resulted in finding that if acrolein-containing gas is introduced into the catalyst layer at a higher temperature than the reaction temperature, the whole catalyst layer is effectively utilized and the yield of acrylic acid from acrolein is raised and that this rise in the yield of acrylic acid is more effectively obtained by controlling the temperature of the reaction layer so that it becomes higher from the inlet side of the gas to the outlet side.

Thus, according to the present invention, provided is a process for subjecting acrolein or acrolein-containing gas to catalytic vapor phase oxidation to produce acrylic acid, characterized by controlling the reaction so that the following equations (1) and (2) are satisfied:

$$1° C. \leq T_0 - T_1 \leq 15° C. \tag{1}$$

$$T_1 < T_2 \tag{2}$$

wherein $T_0$ represents a temperature of acrolein or the acrolein-containing gas in an inlet of a catalyst layer; $T_1$ represents a temperature in an inlet part of the catalyst layer; and $T_2$ represents a temperature in an outlet part of the catalyst layer.

EMBODIMENT OF THE INVENTION

Either acrolein obtained by organic synthesis or acrolein-containing gas obtained by subjecting propylene to catalytic vapor phase oxidation in, for example, a two-step reaction may be used for a starting material used in the present invention. This acrolein-containing gas includes gas obtained by adding thereto, if necessary, oxygen (air), steam and substantially inert gas and gas obtained by separating acrolein and then adding thereto oxygen (air), steam and substantially inert gas. For the sake of convenience, they are hereinafter called generically acrolein-containing gas to explain the present invention.

FIG. 1 is a schematic diagram for explaining the temperature ($T_0$) of the acrolein-containing gas in the inlet of the catalyst layer, the temperature ($T_1$) in the inlet part of the catalyst layer and the temperature ($T_2$) in the outlet part of the catalyst layer, wherein 1 represents a catalyst-filled layer, and 2 represents a heat transfer medium surrounding the catalyst-filled layer.

The temperature ($T_1$) in the inlet part of the catalyst layer and the temperature ($T_2$) in the outlet part of the catalyst layer mean respectively the temperatures of the heat transfer media adjacent to the inlet part of the catalyst layer and the outlet part of the catalyst layer. The inlet part of the catalyst layer and the outlet part of the catalyst layer mean respectively areas falling in a range of 200 mm from the inlet end of the catalyst layer and the outlet end of the catalyst layer, and the temperatures of the heat transfer media adjacent thereto mean the average temperatures of the heat transfer media in these areas.

The present invention is characterized by that the temperature ($T_0$) of the acrolein-containing gas in the inlet of the catalyst layer is elevated by 1 to 15° C., preferably 2 to 10° C. higher than the temperature ($T_1$) in the inlet part of the catalyst layer ($T_0-T_1=1$ to 15° C., preferably 2 to 10° C.) and that the temperature ($T_2$) in the outlet part of the catalyst layer is elevated higher, preferably 1 to 10° C. higher than the temperature ($T_1$) in the inlet part of the catalyst layer ($T_1<T_2$, preferably $T_2-T_1=1$ to 10° C.).

If $T_0-T_1$ is lower than 1° C., the sufficiently high yield of acrylic acid is not obtained, and if it exceeds 15° C., the yield of acrylic acid is rather reduced. Further, in the case of $T_1 \geq T_2$, the sufficiently high yield of acrylic acid is not obtained.

A process for producing acrylic acid from propylene according to a two-step method comprises usually a former step in which propylene is subjected to vapor phase oxidation in the presence of an oxidation catalyst to produce acrolein-containing gas, a cooling step in which the acrolein-containing gas fed from the former step is quenched to prevent an after reaction of acrolein and a latter step in which the acrolein-containing gas is subjected to vapor phase oxidation in the presence of an oxidation catalyst to obtain acrylic acid. In the case of such two-step reaction method, $T_0$, $T_1$ and $T_2$ are controlled in the latter step according to the present invention.

Conditions in carrying out this two-step reaction shall not specifically be restricted, and the reaction can be carried out according to conditions usually used. A shell and tube type fixed bed reactor is usually used for the reactor. In addition thereto, a fixed bed reactor such as a plate heat transfer type reactor can be used as well. Carbon steel and stainless steel which are usually used can be used for a material of the reactor.

One specific example of the oxidation catalyst used in the former step includes a catalyst represented by the following formula (1):

$$Mo_aBi_bFe_cA_dB_eC_fD_gO_x \qquad (1)$$

wherein Mo represents molybdenum; Bi represents bismuth; Fe represents iron; A represents at least one element selected from cobalt and nickel; B represents at least one element selected from alkaline metal, alkaline earth metal and thalium; C represents at least one element selected from tungsten, silicon, aluminum, zirconium and titanium; D represents at least one element selected from phosphorus, tellurium, antimony, tin, cerium, lead, niobium, manganese, arsenic and zinc; O represents oxygen; and when a is 12, b is 0.1 to 10; c is 0.1 to 20; d is 2 to 20; e is 0.001 to 10; f is 0 to 30; g is 0 to 4; and x is a value determined by the oxidation conditions of the respective elements.

Further, one specific example of the latter step catalyst used in the latter step includes a catalyst represented by the following formula (2):

$$Mo_aV_bA_cB_dC_eD_fO_x \qquad (2)$$

wherein Mo represents molybdenum; V represents vanadium; A represents at least one element selected from copper, cobalt, bismuth and iron; B represents at least one element selected from antimony, tungsten and niobium; C represents at least one element selected from silicon, aluminum, zirconium and titanium; D represents at least one element selected from alkaline metal, alkaline earth metal, thalium, phosphorus, tellurium, tin, cerium, lead, manganese and zinc; O represents oxygen; and when a is 12, b is 0.1 to 10; c is 0.1 to 20; d is 0.1 to 20; e is 0.001 to 10; f is 0 to 30; and x is a value determined by the oxidation conditions of the respective elements.

In general, the acrolein-containing gas coming from the former step has a temperature of 300° C. or higher and therefore is usually quenched to 200 to 250° C. in the cooling step in order to prevent an after-oxidation of acrolein. Subsequently, an oxidation reaction is carried out usually at a temperature of 250 to 300° C. in the latter step.

A method for controlling the temperature ($T_0$) of the acrolein-containing gas in the inlet of the catalyst layer and the temperature ($T_1$) in the inlet part of the catalyst layer to 1° C.$\leq T_0-T_1 \leq$15° C., preferably 2° C.$\leq T_0-T_1 \leq$10° C. in the latter step shall not specifically be restricted. There can be employed, for example, (1) a method in which the acrolein-containing gas is heated again by usually used preheating operation such as heat exchange, (2) a method in which the degree of cooling in the cooling step is controlled (that is, controlled so that the gas is not cooled too much) and then the acrolein-containing gas is heated again in the same manner as in (1) (this can reduce energy loss) and (3) a method in which a new heating means is provided to heat again the acrolein-containing gas.

Further, a method for controlling the temperature ($T_1$) in the inlet part of the catalyst layer and the temperature ($T_2$) in the outlet part of the catalyst layer to $T_1<T_2$, preferably 1° C.$\leq T_2-T_1 \leq$10° C. shall not specifically be restricted as well and includes various methods. There can be suitably be selected, for example, (1) a method in which a circulating amount of molten salt as a heat transfer medium is varied, (2) a method in which the circulating amount is varied by taking out a heat transfer medium in the middle and (3) a method in which a heat transfer medium is introduced from the inlet part of the catalyst layer and taken out from the outlet part.

According to the present invention, the whole catalyst layer can effectively be used, and therefore the sufficiently high yield of acrylic acid can be obtained even if the temperature ($T_1$) in the inlet part of the catalyst layer is set lower, for example, by 1 to 10° C. as compared with those of conventional methods. This can reduce heating energy required for heating again the acrolein-containing gas.

The present invention has been explained based on the two-step reaction method, but the present invention shall not be restricted thereto. The present invention can be applied as well to a production process for acrylic acid in which a former step reaction for obtaining mainly acrolein by a catalytic vapor phase oxidation of propylene or propylene-containing gas and a latter step reaction for obtaining acrylic acid by a catalytic vapor phase oxidation of acrolein-containing gas are carried out in a single reactor. In this case, the effects of the present invention can be obtained by controlling the temperature ($T_0$) of the acrolein-containing gas in the inlet of the catalyst layer, the temperature ($T_1$) in the inlet part of the catalyst layer and the temperature ($T_2$) in the outlet part of the catalyst layer in the latter step reaction in the manner described above.

EFFECTS OF THE INVENTION

According to the present invention as described above, acrylic acid can be produced stably at a high yield over a long period of time as shown in the following examples.

EXAMPLES

The present invention shall more specifically be explained below with reference to examples. A propylene conversion, an acrolein yield and an acrylic acid yield were determined according to following equations:

propylene conversion (mol %)=(number of mols of propylene reacted)/(number of mols of propylene fed)×100 acrolein yield (mol %)=(number of mols of acrolein produced)/(number of mols of propylene fed)×100 acrylic acid yield (mol %)=(number of mols of acrylic acid produced)/(number of mols of propylene fed)×100

Preparation Example 1

(a) Preparation of Catalyst for Former Step Reaction

Ammonium molybdate 1062 g and ammonium paratungstate 270 g were dissolved in 1500 ml of distilled water while stirring under heating (a resulting solution is called a solution I). Separately, a solution obtained by dissolving 700 g of cobalt nitrate in 200 ml of distilled water, a solution obtained by dissolving 243 g of ferric nitrate in 200 ml of distilled water and a solution obtained by dissolving 292 g of bismuth nitrate in 300 ml of distilled water to which 60 ml of conc. nitric acid was added to acidity were mixed to prepare a nitrate solution (this is called a solution II). The solution II was dropwise added to the solution I, and then a solution obtained by dissolving 1.68 g of potassium hydroxide in 150 ml of distilled water and 226 g of a 20% silica sol solution were added thereto. A suspension thus obtained was stirred while heating to be evaporated and dried, and then the residue was molded into pellets having a diameter of 5 mm. The pellets were baked under a flow of air at a maximum temperature of 450° C. for 6 hours to thereby obtain a catalyst for a former step reaction. This catalyst for a former step reaction had the following composition ratio excluding oxygen:

$Co_{4.8}Fe_{1.2}Bi_{1.2}W_{1.0}Mo_{12}Si_{1.5}K_{0.06}$ (b) Preparation of Catalyst for Latter Step Reaction Ammonium molybdate 1014 g, ammonium paratungstate 323 g and ammonium metavanadate 224 g were dissolved in 3000 ml of distilled water while stirring under heating. A solution obtained by dissolving 231 g of copper nitrate in 500 ml of distilled water and 38 g of titanium oxide were put into this solution to thereby obtain a suspension. A commercially available silica-alumina carrier 1000 ml having a particle diameter of 4 to 5 mm and a specific surface area of 1 m²/g or less was added to this suspension, and the mixture was evaporated and dried while stirring, whereby the catalyst components were supported on the carrier. Then, it was baked under an aerial atmosphere at 400° C. for 6 hours to thereby obtain a catalyst for a latter step reaction. This catalyst for a latter step reaction had the following composition ratio excluding oxygen:

$Mo_{12}V_4W_{2.5}Cu_2Ti_3$

Example 1

(a) Former Step Reaction

A stainless steel-made reaction tube having an inner diameter of 25 mm and a length of 4200 mm which was dipped in a molten salt bath held at substantially even temperature was charged with the catalyst for a former reaction obtained in the preparation example so that the layer length was 3000 mm. A reaction gas comprising 6 vol % of propylene, 60 vol % of air and the balance of steam was fed into this reaction tube at a space velocity of 2000 (1/hr) to carry out the reaction at a salt bath temperature of 325° C. In this case, the gas had a temperature of 332° C. in the outlet of the reaction tube, and the following results were obtained:

| Propylene conversion rate | 95.8 mol % |
| Acrolein yield | 78.5 mol % |
| Acrylic acid yield | 12.8 mol % |

(b) Latter Step Reaction

A stainless steel-made reaction tube having an inner diameter of 25 mm and a length of 4200 mm which was dipped in a circulatable molten salt bath was charged with the catalyst for a latter reaction obtained in the preparation example so that the layer length was 3000 mm. The gas mixture obtained in the former step reaction described above was fed, after cooled down to a prescribed temperature ($T_0$), into this reaction tube at a space velocity of 2000 (1/hr) to carry out the reaction. The gas temperature ($T_0$) in the inlet of the catalyst layer, the temperature ($T_1$) in the inlet part of the catalyst layer and the temperature ($T_2$) in the outlet part of the catalyst layer were controlled to values shown in Table 1 in carrying out the reaction. The overall results of the former step reaction and the latter step reaction are shown in Table 1. The temperature $T_2$ was controlled by varying the circulating amount of the molten salt.

Examples 2 to 5

The same procedure as in Example 1 was repeated to carry out the reaction, except that the gas temperature ($T_0$) in the inlet of the catalyst layer, the temperature ($T_1$) in the inlet part of the catalyst layer and the temperature ($T_2$) in the outlet part of the catalyst layer were controlled to values shown in Table 1 to carry out the latter step reaction. The overall results of the former step reaction and the latter step reaction are shown in Table 1.

TABLE 1

| Example | $T_0$ (° C.) | $T_1$ (° C.) | $T_2$ (° C.) | Propylene conversion (mol %) | Acrolein yield (mol %) | Acrylic acid yield (mol %) |
| --- | --- | --- | --- | --- | --- | --- |
| 1 | 273 | 263 | 265 | 96.0 | 0.4 | 88.4 |
| 2 | 270 | 265 | 266 | 96.2 | 0.8 | 88.0 |
| 3 | 275 | 264 | 266 | 96.1 | 0.2 | 88.2 |
| 4 | 275 | 262 | 264 | 95.9 | 0.3 | 88.2 |
| 5 | 275 | 263 | 268 | 96.2 | 0.2 | 88.3 |

Comparative Examples 1 to 4

The same procedure as in Example 1 was repeated to carry out the reaction, except that the gas temperature ($T_0$) in the inlet of the catalyst layer, the temperature ($T_1$) in the inlet part of the catalyst layer and the temperature ($T_2$) in the outlet part of the catalyst layer were controlled to values shown in Table 2 to carry out the latter step reaction. The overall results of the former step reaction and the latter step reaction are shown in Table 2.

TABLE 2

| Comparative Example | $T_0$ (° C.) | $T_1$ (° C.) | $T_2$ (° C.) | Propylene conversion (mol %) | Acrolein yield (mol %) | Acrylic acid yield (mol %) |
| --- | --- | --- | --- | --- | --- | --- |
| 1 | 283 | 263 | 265 | 96.2 | 0.1 | 85.0 |
| 2 | 265 | 265 | 265 | 96.1 | 1.6 | 86.0 |
| 3 | 265 | 265 | 278 | 96.3 | 0.5 | 85.6 |
| 4 | 274 | 265 | 260 | 96.0 | 1.4 | 86.6 |

The values of $T_0-T_1$ are 20° C., 0° C. and 0° C. respectively in Comparative Examples 1 to 3. It can be found from the results shown in Table 2 that when the reaction is not controlled so that the condition of $T_0-T_1=1$ to 15° C. is not satisfied, the acrylic acid yield is low.

Further, the values of $T_2-T_1$ is −5° C. in Comparative Example 4. It can be found from the results shown in Table 2 that the acrylic acid yield is low in the reaction under the condition of $T_2<T_1$.

Example 6

In Example 1, the gas temperature ($T_0$) in the inlet of the catalyst layer, the temperature ($T_1$) in the inlet part of the catalyst layer and the temperature ($T_2$) in the outlet part of the catalyst layer were controlled to values shown in Table 3 to continue the oxidation reaction for 12000 hours. The overall results of the former step reaction and the latter step reaction are shown in Table 3.

Comparative Example 5

In Comparative Example 1, the gas temperature ($T_0$) in the inlet of the catalyst layer, the temperature ($T_1$) in the inlet part of the catalyst layer and the temperature ($T_2$) in the outlet part of the catalyst layer were controlled to values shown in Table 3 to continue the oxidation reaction for 4000 hours. The overall results of the former step reaction and the latter step reaction are shown in Table 3.

TABLE 3

| Example | Reaction Time | $T_0$ (° C.) | $T_1$ (° C.) | $T_2$ (° C.) | Propylene conversion (mol %) | Acrolein yield (mol %) | Acrylic acid yield (mol %) |
| --- | --- | --- | --- | --- | --- | --- | --- |
| Example 6 | A | 273 | 263 | 265 | 96.0 | 0.4 | 88.4 |
|  | B | 278 | 268 | 270 | 96.2 | 0.4 | 88.3 |
| Comparative Example 5 | A | 283 | 263 | 265 | 96.2 | 0.1 | 85.0 |
|  | C | 288 | 268 | 270 | 96.3 | 1.2 | 84.4 |

A: Beginning of reaction
B: After 12000 hours
C: After 4000 hours

It can be found from the results shown in Table 3 that when the reaction is controlled so that the conditions of $T_0-T_1=1$ to 15° C. and $T_1<T_2$ are satisfied (Example 6), acrylic acid can stably be produced at a high yield over a long period of time as compared with the case in which the reaction is not controlled in such manner (Comparative Example 5).

What is claimed is:

1. A process for subjecting acrolein or acrolein-containing gas to catalytic vapor phase oxidation to produce acrylic acid in a reactor having an inlet and an outlet, comprising, controlling he reaction so that the following equations (1) and (2) are satisfied:

$$1° C. \leq T_0-T_1 \leq 15° C. \quad (1)$$

$$T_1<T_2 \quad (2)$$

wherein $T_0$ represents a temperature of acrolein or the acrolein-containing gas fed to the inlet of the reactor; $T_1$ represents a temperature in an inlet part of the catalyst layer; and $T_2$ represents a temperature in an outlet part of the catalyst layer.

2. The process as described in claim 1, wherein the reaction is controlled so that the following equations (1) and (2) fire satisfied:

$$2° C. \leq T_0-T_1 \leq 10° C. \quad (1)$$

$$1° C. \leq T_2-T_1 \leq 10° C. \quad (2).$$

3. A process for forming acrylic acid by the vapor phase catalytic oxidation of acrolein in an acrolein containing gas in a reaction zone having an inlet part and an outlet part and comprising a layer of oxidation catalyst for the vapor phase catalytic oxidation of acrolein, said process comprising
feeding acrolein or an acrolein containing gas to said reaction zone while maintaining the temperature of the acrolein or acrolein-containing gas at a temperature $T_0$,
maintaining the temperature of the inlet part of the reaction zone at a temperature $T_1$,
wherein 1° C. $\leq T_0-T_1 \leq$ 15° C., and
maintaining the temperature of the outlet part of the reaction zone at a temperature $T_2$,
wherein $T_2>T_1$.

4. The process according to claim 3, wherein the temperatures $T_0$, $T_1$, and $T_2$, are maintained such that, $$2° C. \leq T_0-T_1 \leq 10° C., \text{ and}$$

$$1° C. \leq T_2-T_1 \leq 10° C.$$

5. The process of claim 1, wherein the step of controlling the reaction comprises heating the acrolein-containing gas to raise its temperature to a temperature which is from 1° C. to 10° C. higher than the temperature $T_1$.

6. The process of claim 1, wherein the acrolein-containing gas is a gas obtained by the vapor phase catalytic oxidation of propylene and, wherein the step of controlling the reaction comprises raising the temperature of the acrolein-containing gas from the vapor phase catalytic oxidation of propylene which has been cooled to a temperature below the temperature at which acrolein will be oxidized to carbon dioxide or carbon monoxide, to a temperature which is from 1° C. to 10° C. higher than the temperature $T_1$.

7. The process of claim 1, wherein the temperatures $T_1$ and $T_2$ are controlled by circulating a heat exchange medium in heat exchange contact with the inlet and outlet parts of the catalyst layer, and wherein step of controlling the reaction comprises circulating varying amounts of the heating medium such that $T_2$ is maintained higher than $T_1$.

8. The process of claim 1, wherein the temperatures $T_1$ and $T_2$ are controlled by circulating a heat exchange medium in heat exchange contact with the inlet and outlet parts of the catalyst layer, and wherein the step of controlling the reaction comprises removing a portion of the heat exchange medium from between the inlet part of the catalyst layer and the outlet part of the catalyst layer.

9. The process of claim 1, wherein the temperatures $T_1$ and $T_2$ are controlled by passing a heat exchange medium in heat exchange contact with the catalyst layer, wherein the step of controlling the reaction comprises introducing the heat exchange medium at the inlet part of the catalyst layer and removing the heat exchange medium from the outlet part of the catalyst layer.

10. The process of claim 3, wherein the step of maintaining the temperature of the acrolein-containing gas at $T_0$, comprises raising its temperature to a temperature which is from 1° C. to 10° C. higher than the temperature $T_1$.

11. The process of claim 3, wherein the acrolein-containing gas is a gas obtained by the vapor phase catalytic oxidation of propylene and wherein the step of maintaining the temperature of the acrolein-containing gas at $T_0$ comprises cooling the acrolein-containing gas from the vapor phase catalytic oxidation of propylene to a temperature below the temperature at which acrolein will be oxidized to carbon dioxide or carbon monoxide, and before introducing the acrolein-containing gas to the inlet part of the catalyst layer, heating the gas to a temperature which is from 1° C. to 10 ° C. higher than the temperature $T_1$.

12. The process of claim 3, wherein the steps of maintaining temperatures $T_1$ and $T_2$ comprise circulating varying amounts of a heat exchange medium in heat exchange contact with the inlet and outlet parts of the catalyst layer such that $T_2$ is maintained higher than $T_1$.

13. The process of claim 3, wherein the steps of maintaining temperatures $T_1$ and $T_2$ comprise circulating a heat exchange medium in heat exchange contact with the inlet and outlet parts of the catalyst layer, and removing a portion of the heat exchange medium from between the inlet part of the catalyst layer and the outlet part of the catalyst layer.

14. The process of claim 3, wherein the steps of maintaining the temperatures $T_1$ and $T_2$ comprise introducing a heat exchange medium in heat exchange contact with the catalyst layer at the inlet part of the catalyst layer and removing the heat exchange medium from the outlet part of the catalyst layer.

* * * * *